United States Patent [19]
Schmieding

[11] Patent Number: 5,391,171
[45] Date of Patent: Feb. 21, 1995

[54] PIN-LOCKED CANNULATED SCREWDRIVER

[75] Inventor: Reinhold Schmieding, Naples, Fla.

[73] Assignee: Arthrex, Inc., Naples, Fla.

[21] Appl. No.: 19,357

[22] Filed: Feb. 18, 1993

Related U.S. Application Data

[63] Continuation-in-part of Ser. No. 836,721, Feb. 19, 1992, Pat. No. 5,211,647.

[51] Int. Cl.⁶ ............................................. A61B 17/58
[52] U.S. Cl. ................................... 606/104; 606/73; 606/96; 606/103
[58] Field of Search ................. 606/88, 73, 86, 96, 606/97, 98, 104, 103, 99; 81/436, 451

[56] References Cited

U.S. PATENT DOCUMENTS

| | | | |
|---|---|---|---|
| 3,351,054 | 2/1965 | Florek | 606/104 |
| 4,877,020 | 10/1989 | Vich | 606/86 |
| 4,927,421 | 5/1990 | Goble | 606/73 |
| 5,049,151 | 9/1991 | Durham | 606/96 |
| 5,139,499 | 8/1992 | Small | 606/73 |
| 5,139,520 | 8/1992 | Rosenberg | 606/96 |
| 5,152,765 | 10/1992 | Ross | 606/104 |

FOREIGN PATENT DOCUMENTS

| | | | |
|---|---|---|---|
| 238724 | 9/1986 | Germany | 606/104 |

*Primary Examiner*—Robert A. Hafer
*Assistant Examiner*—David J. Kenealy
*Attorney, Agent, or Firm*—Ostrolenk, Faber, Gerb & Soffen

[57] ABSTRACT

A pin-locked cannulated screwdriver assembly and method for the endosteal fixation of a graft by screw insertion by drilling a graft tunnel through adjacent bone masses and extending a graft attached between bone blocks under tension in the graft tunnel. A guide pin is secured within a cannulated screwdriver. The guide pin includes a mark for indicating the depth of insertion of an end of the pin. Using the screwdriver, the guide pin can be positioned between one of the cut bone blocks and one of the adjacent bone masses. The cannulated screwdriver is removed from the guide pin, with the guide pin remaining positioned between the one bone block and bone mass. A cannulated interference screw is positioned on the distal end of the screwdriver and the screwdriver and screw are slid over the positioned guide pin. The position of the cannulated screwdriver over the guide pin is then locked. Alternatively, the screwdriver can be locked over the guide pin initially, with the position of the guide pin adjusted so that end of the pin including the marking extends from the screwdriver. The cannulated interference screw is then positioned at the distal end of the screwdriver, and the entire assembly is inserted between the bone block and bone mass.

4 Claims, 5 Drawing Sheets

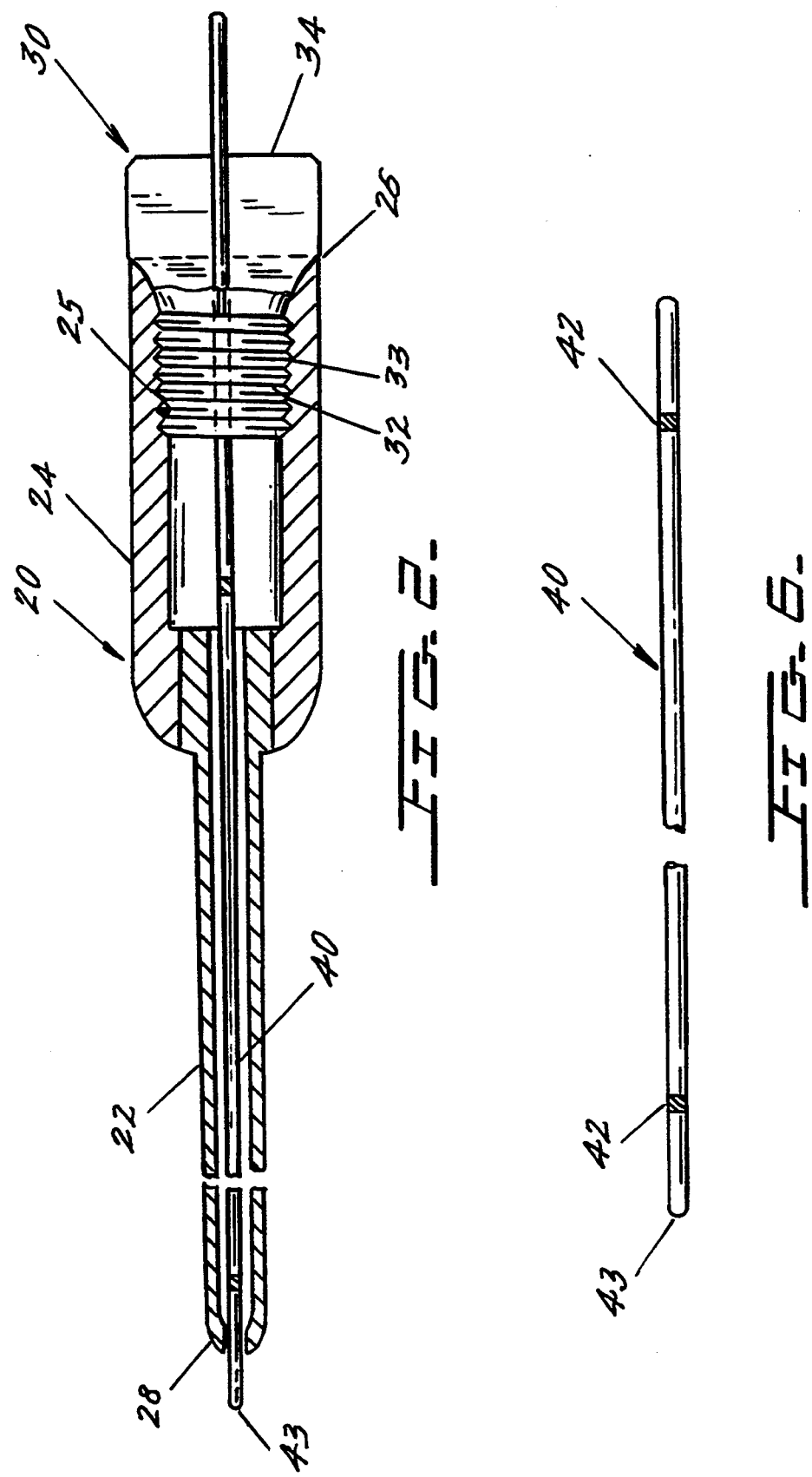

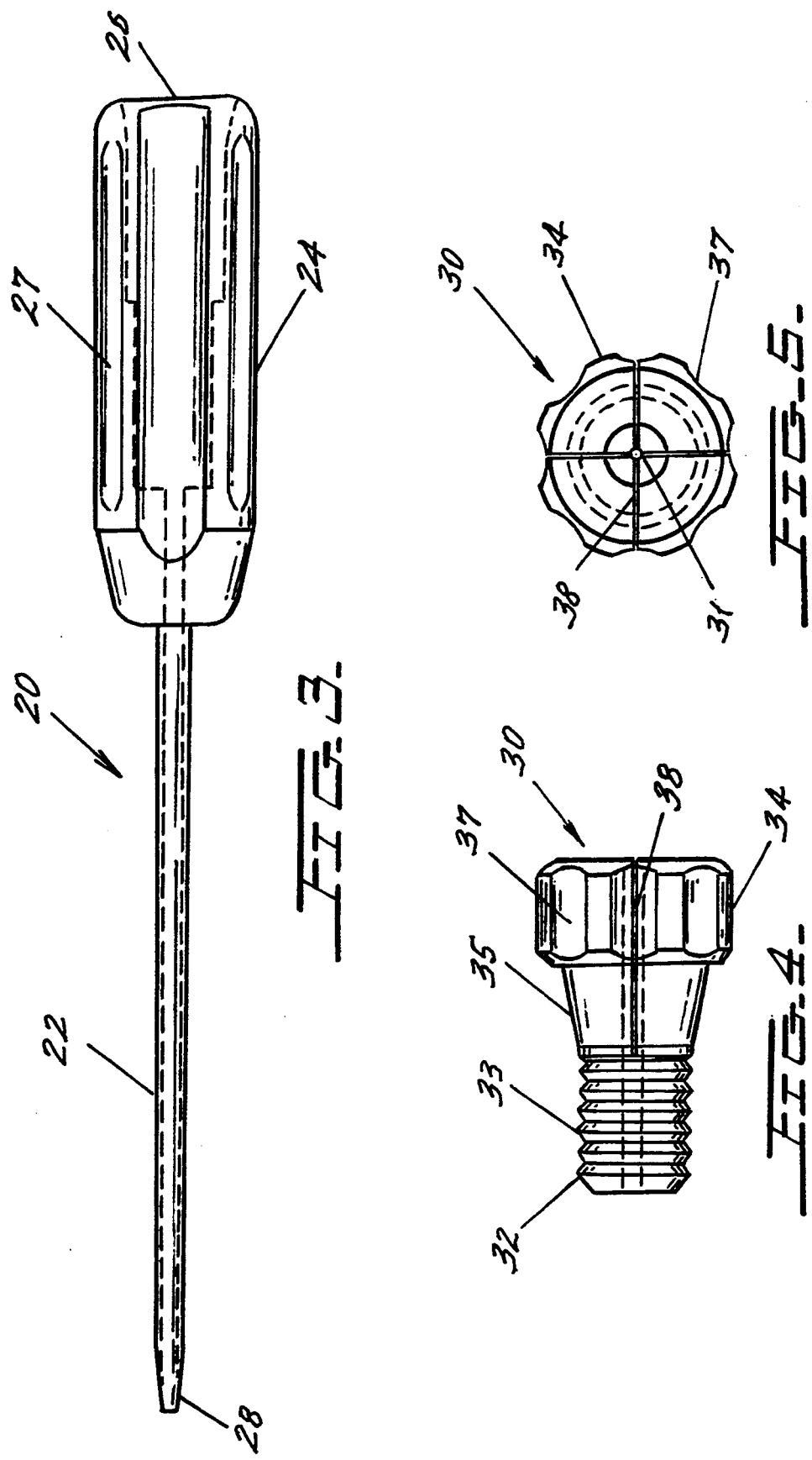

PIN-LOCKED CANNULATED SCREWDRIVER

This is a continuation-in-part of U.S. application Ser. No. 07/836,721, filed Feb. 19, 1992, now U.S. Pat. No. 5,211,647.

BACKGROUND OF THE INVENTION

1. Field of the Invention

The present invention relates to a cannulated screwdriver for arthroscopic surgery and, more specifically, to a pin-lock cannulated screwdriver which can be fixed in relation to a guide pin during endosteal fixation of a ligament by screw insertion.

2. Description of the Related Art

Endosteal fixation of a substitute ligament or graft is well known in the art. See, e.g., Kurosaka, et al., "*A Biochemical Comparison of Different Surgical Techniques of Graft Fixation in Anterior Cruciate Ligament Reconstruction*," Am. Jour. Sports Med., Vol. 15, No. 3, pp. 225-229 (1987). When a ligament or tendon becomes detached from a bone, surgery is usually required to resecure the ligament or tendon. Often, a substitute ligament or graft is attached to the bone to facilitate regrowth and permanent attachment. Various methods of graft attachment are known, such as staples and sutures over buttons. However, such methods often do not provide a sufficiently strong attachment to withstand the normal tensile loads to which they are subjected.

A stronger graft attachment is obtained by using an interference screw to wedge a graft bone block to the wall of a graft tunnel formed through the bone. FIG. 1 illustrates this method, in which the graft 2, with bone blocks 4,6 at each end, is pulled through a graft tunnel 8 in the tibia 10 by applying a tensile force on sutures 12 attached to leading bone block 6. The leading bone block 6 is brought forward into the femur 14 until it is fully nested in a graft tunnel in the femur. Then, with tension applied to the graft 2 via sutures 12, a screwdriver is used to insert interference screws 16 between the bone blocks 4,6 and the graft tunnel, first in the femur and then in the tibia.

A guide pin is often used in conjunction with a cannulated interference screw (and a cannulated screwdriver) to properly locate the screw against the bone block. However, inserting the guide pin is cumbersome, because the pin tends to bend and is difficult to grip. Moreover, even when the guide pin is properly located, the surgeon has to eye the correct depth of the insertion of the pin. Also, handling the guide pin and screwdriver as separate pieces is inconvenient during surgery.

SUMMARY OF THE INVENTION

The present invention overcomes the above-noted deficiencies of the prior art by providing a cannulated screwdriver which can be secured to a guide pin, such that the screwdriver can be used to assist the surgeon in inserting the guide pin within the guide tunnel. An etched marking on the end of the guide pin assists the surgeon in gauging the correct depth of insertion of the pin. Thereafter, the screwdriver can be removed and an interference screw placed on the end of the screwdriver. The screwdriver and cannulated interference screw can be inserted over the seated guide pin, the interference screw can be screwed in place, and the pin and screwdriver removed.

The invention also provides a screwdriver and guide pin which can be assembled together for one step insertion of an interference screw. In this procedure, the guide pin is inserted through the screwdriver, with the etched marking of the guide pin being exactly at the end of the screwdriver. The screwdriver and the guide pin are then secured together in this position. The interference screw can then be slid over the end of the guide pin extending from the screwdriver. The guide pin is then inserted into the tibial tunnel using the screwdriver as a handle, and the interference screw is screwed between the bone block and the knee using the screwdriver.

The present invention advantageously reduces the number of parts to be handled by the surgeon. Since the guide pin is locked with respect to the screwdriver, the surgeon needs only one hand to support the screwdriver and guide pin assembly.

Preferably, a cannulated locking nut is used to secure the cannulated screwdriver of the invention to the guide pin. The locking nut includes threads which mate with threads provided on an interior part of the screwdriver handle. The locking nut preferably includes a plurality of slots extending axially therethrough. The slots allow the nut to be compressed when the nut is threaded into the screwdriver handle, thereby securing the nut onto the guide pin.

Other features and advantages of the present invention will become apparent from the following description of the invention which refers to the accompanying drawings.

BRIEF DESCRIPTION OF THE DRAWINGS

FIG. 2 is a cross-sectional view of the pin-lock cannulated screwdriver assembly of the present invention.

FIG. 3 is a side view of the cannulated screwdriver.

FIG. 4 is a side view of the locking nut of the present invention.

FIG. 5 is a top view of the locking nut of FIG. 4.

FIG. 6 illustrates the guide pin of the present invention.

DETAILED DESCRIPTION OF THE PREFERRED EMBODIMENT

Figure 1:
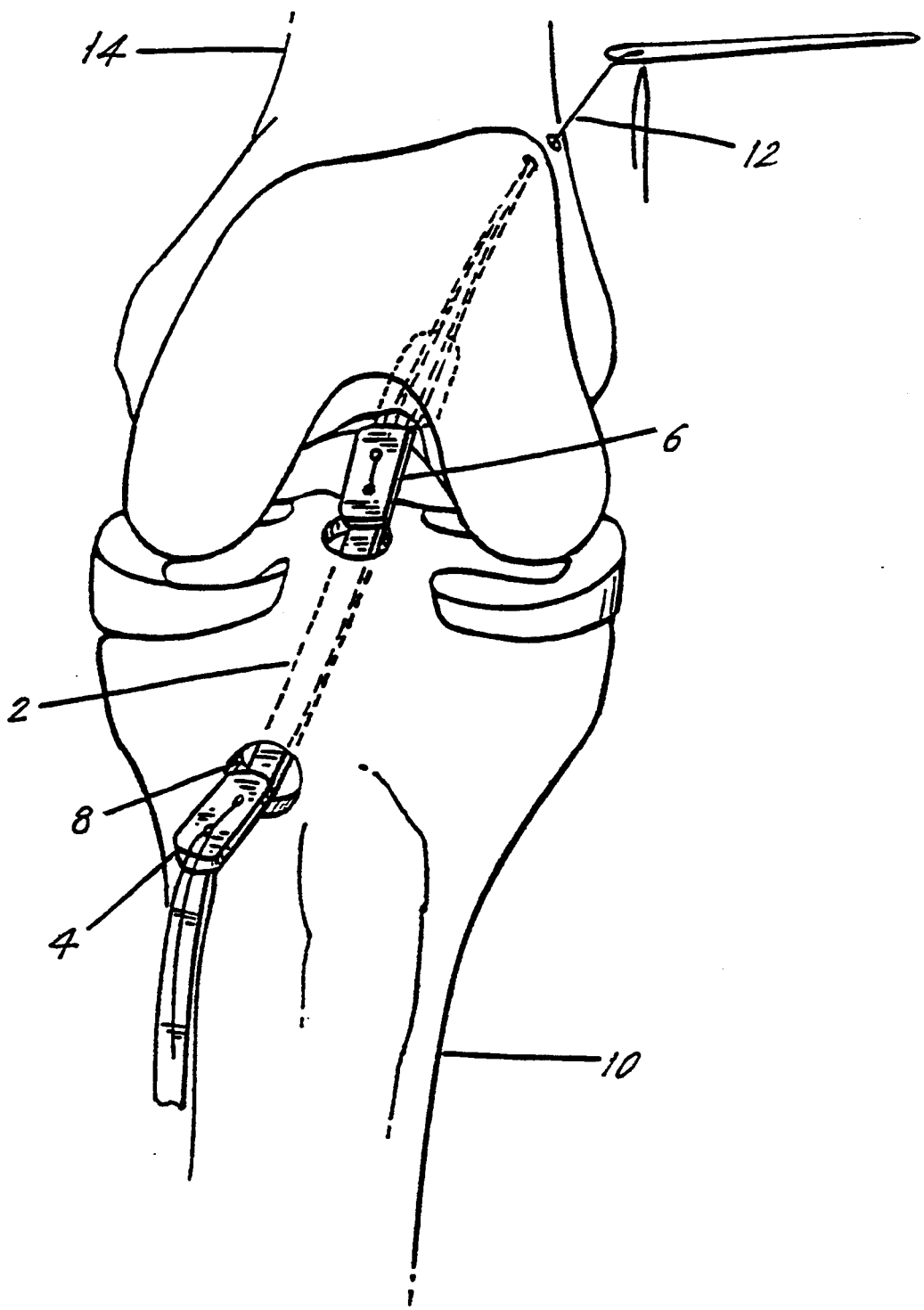
FIG. 1 illustrates a graft stretched between two bone blocks being positioned in a graft tunnel.

Referring to FIGS. 2 and 3, the pin-lock screwdriver assembly of the present invention includes cannulated screwdriver 20. Screwdriver 20 consists of shaft 22 and handle 24. Preferably, the shaft 22 has an outer diameter of 3.5 mm. and is made of stainless steel for added strength.

Handle 24 is preferably aluminum and has an outer diameter which corresponds generally to the outer diameter of nut 30, discussed below. Handle 24 has a proximal end 26 provided with inner threads 25. Preferably, the threads 25 extend over a length of approximately 22 mm. The inner diameters of shaft 22 and handle 24 are just large enough to accommodate guide pin 40. The proximal end of the shaft 22 is embedded within handle 24 and the distal end 28 is open for the guide pin 40 to extend outward. Handle 24 also includes axially extending flutes 27 spaced along its circumference to facilitate gripping by the user.

As shown in FIGS. 4 and 5, locking nut 30 includes head 34 and shaft 32 provided with threads 33. Preferably, the nut is approximately 50 mm long and head 34 has an outer diameter of approximately 30 mm. Referring back to FIG. 2, shaft 32 extends through proximal end 26 of handle 24 and mates with threads 25 of handle 24. A bore 31 is disposed through locking nut 30 to receive guide pin 40. Bore 31 is preferably designed to accommodate a 2 mm guide pin.

Nut shaft 32 and head 34 are bridged by angled neck 35. Slots 38 extend axially from head 34 through neck 35. A plurality of slots 38 are disposed around the circumference of the nut, preferably one slot every 90 degrees. In operation, pin 40 is inserted into bore 31 of nut 30 and its position therein is adjusted. The nut and pin are screwed into open end 26 of handle 24. As the nut is tightened, slots 38 compress to secure the pin 40 within the nut and screwdriver. The position of the distal end 43 of the pin with respect to end 28 of the screwdriver can also be adjusted by turning nut 30 within handle 24. Head 34 includes flutes 37 for gripping and turning the nut.

Figure 7:
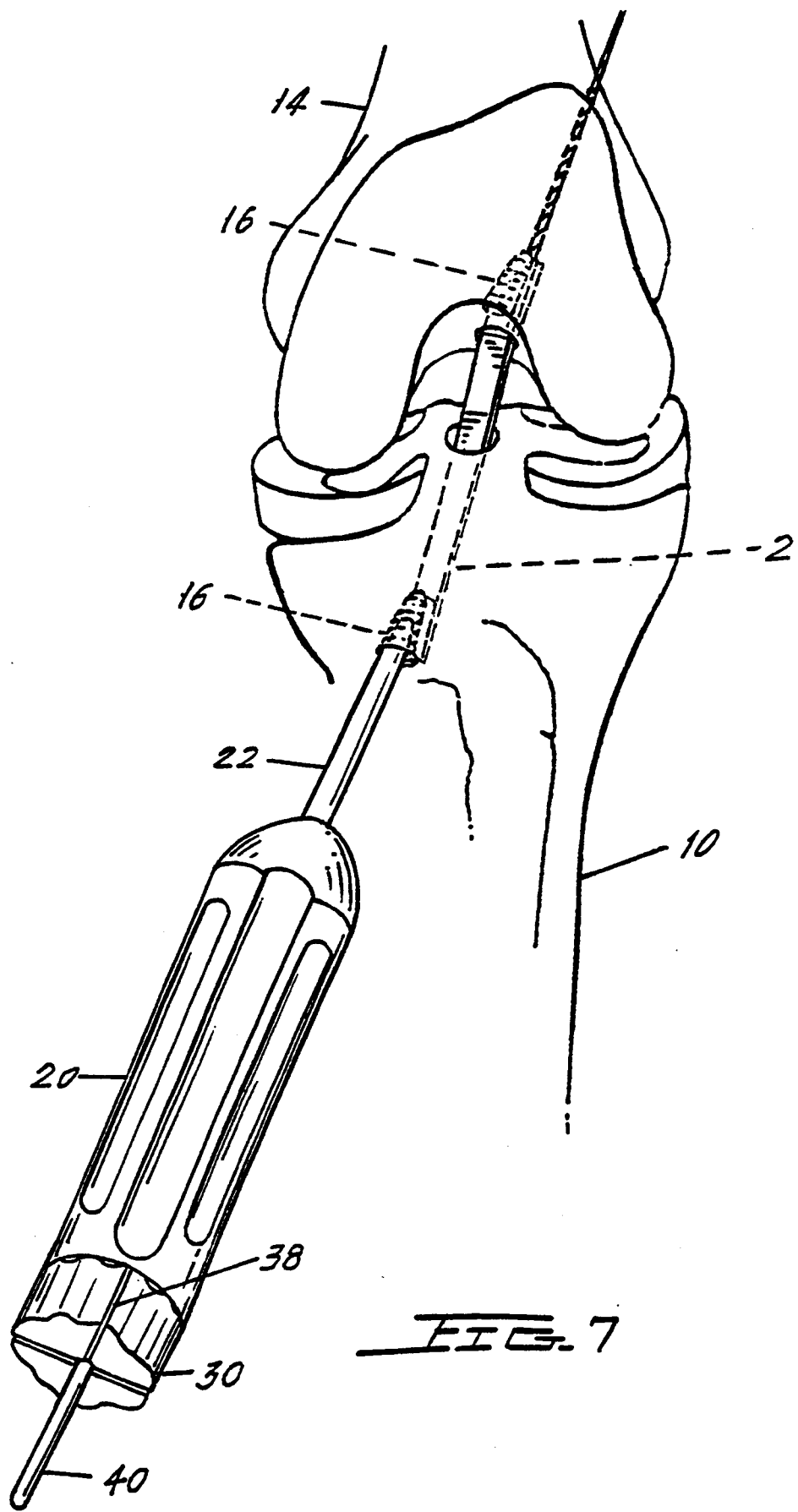
FIG. 7 illustrates an interference screw being driven between the bone mass and the corresponding bone block using the pin-lock screwdriver assembly of the present invention.

Referring to FIG. 6, guide pin 40 includes laser etched markings 42, preferably spaced 25 mm. from each end of the pin. The etched markings 42 allow the surgeon to fix the guide pin within the knee at the desired position. Initially, guide pin 40 can be secured within the locking nut and cannulated screwdriver, and the assembly can be used to insert the guide pin within the guide tunnel. The etched marking 42 on the distal end of the guide pin indicates to the surgeon when the pin has been inserted to the proper depth. Thereafter, the screwdriver is removed and an interference screw 16 placed on the end of the screwdriver, as shown in FIG. 7. The screwdriver and cannulated interference screw are inserted over the placed guide pin, the interference screw can be screwed in place and the pin and screwdriver removed. When the screwdriver is rotated to fix the interference screw between the bone mass and bone block, the guide pin also rotates without any adverse affect on placement.

The screwdriver assembly also advantageously acts as a pin remover. Once the interference screw is in place, the tip of the screwdriver and the guide pin can be removed in one step.

In another application, the screwdriver and guide pin are used together in a one step interference screw insertion procedure. Referring to FIG. 2, the guide pin 40, after being inserted in the locking nut, is inserted through the cannulated screwdriver, with the etched marking of the guide pin being exactly at the end of the screwdriver. The screwdriver and guide pin are then secured together with the locking nut. The cannulated interference screw is then slid over the distal end of the guide pin. Using the screwdriver as a handle, the screw is then inserted in the tibial tunnel and screwed between the bone block and the knee.

Figure 8:
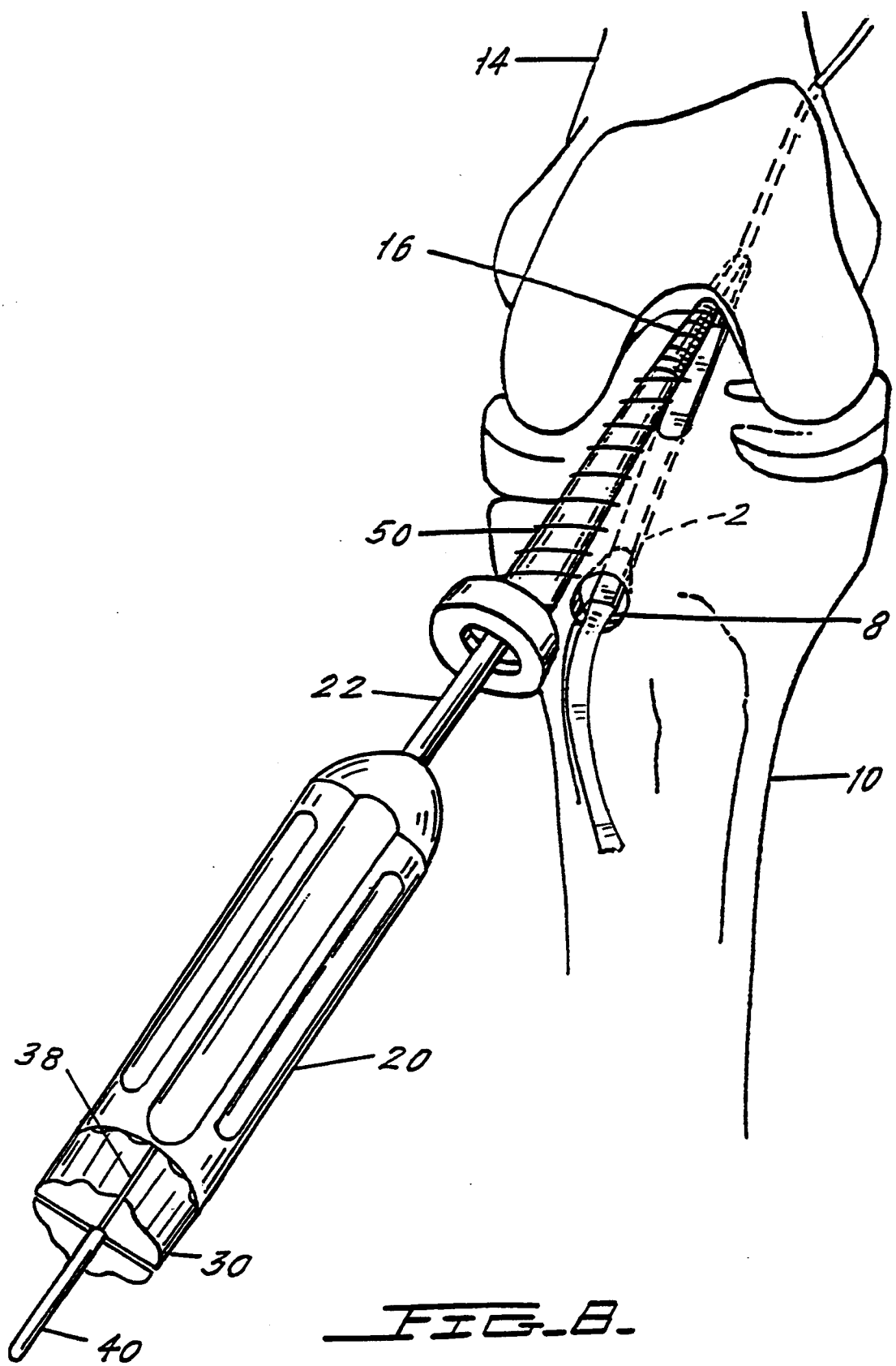
FIG. 8 shows the pin-lock screwdriver assembly of the present invention being used with a cannulated sheath.

As shown in FIG. 8, the shaft 22 of the screwdriver is thin enough to be accommodated within a plastic cannulated sheath 50. Sheath 50 protects the ligament during insertion of the interference screw. See allowed co-pending U.S. patent application Ser. No. 07/836,721, assigned to the same assignee as the present application, for an example of a preferred sheath.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of endosteal fixation of a graft by screw insertion, comprising the steps of:
   drilling a graft tunnel through adjacent bone masses;
   extending a graft attached between bone blocks under tension in said graft tunnel between said adjacent bone masses;
   inserting a guide pin into a cannulated screwdriver, said screwdriver including locking means for releasably securing said guide pin to prevent longitudinal movement of said guide pin relative to said screwdriver, and an elongated shaft for preventing bending of said guide pin;
   releasably securing said cannulated screwdriver to said guide pin with said locking means, adjusting the position of said pin within said screwdriver and locking said guide pin with said locking means;
   inserting said guide pin into said graft tunnel between one of said bone blocks and one of said adjacent bone masses using said screwdriver as a handle;
   releasing and removing said cannulated screwdriver from said guide pin, said guide pin remaining positioned between said one bone block and bone mass;
   positioning a cannulated interference screw on a distal end of said screwdriver;
   sliding said screwdriver and interference screw over said positioned guide pin;
   securing said cannulated screwdriver onto said guide pin;
   driving said interference screw between said one bone mass and bone block with said cannulated screwdriver secured to said guide pin; and
   removing said cannulated screwdriver and guide pin.

2. The method of claim 1, further comprising the step of inserting said screwdriver and interference screw into a cannulated sheath, prior to the step of driving said interference screw.

3. A method of endosteal fixation of a graft by screw insertion, comprising the steps of:
   drilling a graft tunnel through adjacent bone masses;
   extending a graft attached between bone blocks under tension in said graft tunnel between said adjacent bone masses;
   inserting a guide pin into a cannulated screwdriver, said screwdriver including locking means for releasably securing said guide pin to prevent longitudinal movement of said guide pin relative to said screwdriver, and an elongated shaft for preventing bending of said guide pin;
   releasably securing said cannulated screwdriver to said guide pin so that a distal end of said pin extends from said screwdriver;
   positioning a cannulated interference screw over said distal end of said pin and on said screwdriver;
   inserting said interference screw, positioned on said screwdriver, and said distal end of said guide pin, into said graft tunnel between one of said bone blocks and one of said adjacent bone masses using said screwdriver as a handle;
   driving said interference screw between said one bone mass and said one bone block while said screwdriver is secured to said guide pin; and
   removing said cannulated screwdriver and guide pin.

4. The method of claim 3, further comprising the step of inserting said screwdriver and interference screw into a cannulated sheath, prior to the step of driving said interference screw.

* * * * *